(12) United States Patent
Goodchild

(10) Patent No.: US 6,204,027 B1
(45) Date of Patent: Mar. 20, 2001

(54) RIBOZYMES HAVING 2'-O SUBSTITUTED NUCLEOTIDES IN THE FLANKING SEQUENCES

(75) Inventor: John Goodchild, Worcester, MA (US)

(73) Assignee: University of Massachusetts Worcester, Worcester, MA (US)

( * ) Notice: Subject to any disclaimer, the term of this patent is extended or adjusted under 35 U.S.C. 154(b) by 0 days.

(21) Appl. No.: 08/987,032

(22) Filed: Dec. 9, 1997

Related U.S. Application Data

(63) Continuation of application No. 08/296,274, filed on Aug. 25, 1994, now abandoned, which is a continuation of application No. 07/842,049, filed on Feb. 26, 1992, now abandoned.

(51) Int. Cl.[7] .............................. C12P 19/34; C12Q 1/68; C07H 21/04
(52) U.S. Cl. ..................... 435/91.31; 435/6; 536/23.1; 536/23.2; 536/24.5
(58) Field of Search ................... 536/23.1, 23.2, 536/24.5, 24.3; 435/440, 375, 91.31, 91.1, 6

(56) References Cited

U.S. PATENT DOCUMENTS 5,334,711 * 8/1994 Sproat et al. ................. 536/24.5
5,698,687 * 12/1997 Eckstein et al. ............... 536/23.1

OTHER PUBLICATIONS

Goodchild, J. & Kohli, V. Ribozyme that cleaves an RNA sequence from human immunodeficiency virus: the effect of flanking sequence on rate. Arch. Biochem. Biophys. (1991), vol. 284. No. 2, pp. 386–391.*
Goodchild, Nucleic Acid Res., 20: 4607–4612, 1992.*
Uhlman et al. Chem. Reviews, 90: 544–579, 1990.*
Maher et al. Nucleic Acid Res., 16: 3341–3358, 1988.*
Goodchild et al., Archives Biochem. Biophys. 263: 401–409, 1988.*
Kutyavin et al., FEBS Letters, 238:35–38, 1988.*
Inoue et al., Nucleic Acid Res., 15: 6131–6148, 1987.*

* cited by examiner

Primary Examiner—George C. Elliott
Assistant Examiner—Jane Tepps
(74) Attorney, Agent, or Firm—Hale and Dorr LLP

(57) ABSTRACT

The present invention provides methods for increasing ribozyme catalytic activity without reducing specificity, which methods comprise contacting an RNA molecule with a ribozyme having a flanking sequence modified to contain 2'-O-substituted nucleotides. The invention also provides ribozymes comprising a flanking sequence modified to contain 2'-O-substituted nucleotides. In addition, the invention provides methods for increasing ribozyme catalytic activity comprising contacting an RNA molecule with a ribozyme having a flanking sequence modified to contain a 2'-O-substituted nucleotide and a facilitator oligonucleotide. The present invention further provides compositions comprising a ribozyme having modified flanking sequences and an effective amount of a facilitator oligonucleotide.

16 Claims, 5 Drawing Sheets

RIBOZYMES HAVING 2'-O SUBSTITUTED NUCLEOTIDES IN THE FLANKING SEQUENCES

This is a continuation of application Ser. No. 08/296,274, filed Aug. 25, 1994, now abandoned, which is a continuation of application Ser. No. 07/842,049, filed Feb. 26, 1992, now abandoned.

BACKGROUND OF THE INVENTION

1. Field of the Invention

This invention relates to ribozymes that cleave RNA. More specifically it reflects the enhancement of ribozyme catalytic activity by modifying ribozyme flanking sequence nucleotides to have substituents on the oxygen at the 2'-position, and by using a facilitator oligonucleotide complementary to an RNA sequence contiguous to the ribozyme.

2. Description of the Related Art

Drugs might be based on RNA catalysts or enzymes (ribozymes) designed to cleave viral or messenger RNA with high specificity at a rapid rate. These requirements historically have been mutually limiting.

Ribozymes consist of a catalytic core having flanking sequences adjacent the core which hybridize to the substrate RNA. The simplest ribozyme is an RNA motif known as a hammerhead.

Among the factors which limit ribozyme activity in cells are the extent of cellular uptake of the ribozyme and the extent of ribozyme degradation by nucleases. Accordingly, ribozymes having increased resistance to nuclease degradation are desired.

Ribozyme specificity depends on the number of base pairs formed between the ribozyme flanking sequences and its RNA substrate. Increased base pairing has been shown to decrease the rate of cleavage. Goodchild and Kohli, Arch. Biochem. Biophys., 284: 386–391 (1991). Goodchild and Kohli studied the cleavage of a sequence from HIV-1 RNA by various hammerhead ribozymes and determined that the rate of cleavage was dependent on the length of the flanking sequence. Shorter sequences were shown to result in weaker binding between the ribozyme and the cleavage products together with increased rate of cleavage. A ribozyme with 12 bases in the flanking sequences cleaved 10 times faster then one with 20 bases.

However, to have the requisite selectivity or specifity, i.e., the ability to discriminate between all RNA molecules in a cell, a ribozyme must form a minimum of about 15 base pairs with the target substrate. This requirement for selectivity limits the rate of cleavage that may be realized.

Accordingly, ribozymes having increased catalytic activity or methods of increasing ribozyme catalytic activity are needed.

Uhlenbeck, Nature, 328: 596–600 (1987) describes the synthesis of two oligoribonucleotides that can combine to form a structure consistent with the consensus self-cleaving domain. Because rapid cleavage of one of the oligomers was observed only when the other was present, the domain was necessary and sufficient for cleavage. The properties of the cleavage reaction were studied in detail. Nearly complete cleavage occurred even with large excess of the oligomer that was cleaved. This indicates that the oligomer that is uncleaved can cycle in the reaction and therefore be considered to act as a catalyst in the cleavage of the other oligomer.

Haseloff and Gerlach, Nature 334: 585–59 (1988), discuss the dissection of the RNA substrate and enzyme activities from a single self-cleaving domain from the (+) strand of the satellite RNA of tobacco ringspot virus (sTobRV). Inspection of the separated substrate and ribozyme activities, in comparison with other naturally-occurring self-cleaving domains, led to a model for the design of oligoribonucleotides which posses new and highly sequence-specific endoribonuclease activities. This model was successfully tested by the design and construction of ribozymes targeted against three sites within the Tn9 chloramphenicol acetyltransferase (CAT) messenger RNA sequence.

Chemical modifications to nucleotides in the central region of various hammerhead ribozymes have been attempted; no such modifications have resulted in increased catalytic activity. In fact, almost all such reported modifications have resulted in decreased catalytic activity for the ribozymes.

Perreault, et al., Nature 344: 565–567 (1990) reports the results of replacing ribonucleotides in a ribozyme with deoxyribonucleotides. Analysis of the cleavage products of several of the hammerhead analogs indicated the involvement and the reaction of the 2'-OH adjacent to the cleavage site in a substrate. This analysis demonstrated that some 2'-OH groups in the catalytic region affect activity. The introduction of 2'-deoxynucleotides at the conserved positions E 13, 14 and 27–29 within the ribozyme sequence resulted in a 96% decrease of catalytic efficiency.

In addition, Perreault et al., Biochemistry 30: 4020–4025 (1991), and Dahn and Uhlenbeck, Biochemistry 72: 819–23 (1990) report that the replacement of various 2'-hydroxyl groups with hydrogen atoms reduced the catalytic activity of hammerhead ribozymes.

Olsen et al., Biochemistry 30: 9735–9741 (1991), report that replacing 2'-hydroxyl groups on all adenosine residues by either fluorine or hydrogen produced a large decrease in catalytic activity.

Pieken et al., Science 253: 314–317 (1991), report that catalytic activity was reduced by replacing various 2'-hydroxyl groups on adenosine residues by fluorine and by replacing the 2'-hydroxyl groups on cytidine residues by amine groups. However, catalytic activity was unaltered by replacing the 2'-hydroxyl groups on cytidine residues by fluorine or the 2'-hydroxyl groups on uridine residues by fluorine or amino groups.

Odai et al., FEBS Letters 267: 150–152 (1990), report that replacing by hydrogen the exocyclic amino group of a conserved guanosine residue in the core region reduced catalytic activity.

Ruffner and Uhlenbeck, Nucleic Acids Research 18: 6025–6029 (1990), and Buzayan et al., Nucleic Acids Research 18: 4447–4451 (1990), disclose that replacing oxygen atoms by sulfur on various internucleotide phosphate residues reduced catalytic activity.

Fedor and Uhlenbeck, Proc. Natl. Acad. Sci. USA 87: 1668–1672 (1990), analyzed the kinetics of cleavage for several hammerhead sequences to characterize the reaction mechanism and explore how nucleotides involved in substrate binding affect cleavage.

Goodchild et al., Arch. Biochem. Biophys. 263: 401–409 (1988) discusses the effects of a series of synthetic oligonucleotides (hybridons) complementary to the 5' non-coding regions of rabbit β-globin mRNA on endogenous protein synthesis in a rabbit reticulocyte cell-free translation system. With highly purified hybridons inhibition was completely specific for beta globin. Mixtures of two oligonucleotides binding contiguously to the mRNA were more effective than either oligomer alone.

Maher and Dolnick, Nucleic Acids Res. 16: 3341–3358 (1988) report that antisense oligonucleotides containing either anionic diester or neutral methylphosphonate internucleoside linkages were prepared by automated synthesis, and subsequently compared for their ability to arrest translation of human dihydrofolate reductase (DHFR) mRNA in a nuclease treated rabbit reticulocyte lysate. In the case of oligodeoxyribonucleotides, tandem targeting of three 14-mers resulted in synergistic and complete selective inhibition of DHFR synthesis at a total oligomer concentration of 25 µM.

Kutyavin et al, FEBS Lett. 238: 35–38 (1988) report that mono- and diphenazinium derivatives of oligonucleotides complementary to the DNA sequence adjacent to the target sequence of the addressed alkylation of DNA significantly enhance the extent and specificity of alkylation by p-(N-2-chloroethyl-N-methylamino(benzylamido) derivatives of the addressing oligonucleotides.

Inoue et al., Nucleic Acids Res. 15: 6131–6148 (1977) determined that (1) a 2'-O-methyl oligodeoxyribonucleotide-RNA duplex was much more stable than the corresponding oligodeoxy ribonucleotide and (2) the 2'-O-methyl oligonucleotide containing duplex was not a substrate for ribonuclease H.

Dunlap et al., Biochemistry, 10: 2581–2587 (1971) evaluated degradation studies using 2'-O-methylated oligonucleotides with a crude cell-free protein synthesizing system known to contain a variety of nucleases and determined the methylated nucleotides conferred nuclease resistance to the polymers. The 2'-O-methylated oligonucleotides were very resistant to mixtures of alkaline phosphatase, snake venom phosphodiesterase, and micrococcal nuclease.

SUMMARY OF THE INVENTION

The present invention provides methods for increasing hammerhead ribozyme catalytic activity which methods comprise introducing into a flanking sequence of the hammerhead ribozyme nucleotide modified to have a substituent on the oxygen at the 2' position, i.e., a 2'-O-substituted nucleotide.

The invention also provides hammerhead ribozymes comprising a flanking sequence nucleotide modified to have a substituent on the oxygen at the 2' position.

In addition, the invention provides methods for increasing ribozyme catalytic activity comprising contacting an RNA molecule with a ribozyme having a flanking sequence nucleotide modified to have a substituent on the oxygen at the 2' position, and a facilitator oligonucleotide.

The present invention further provides compositions comprising a ribozyme having modified flanking sequences and an effective amount of a facilitator oligonucleotide.

The present invention also provides ribozymes comprising a flanking sequence modified to contain 2'-O-alkyl or acyl nucleotides.

DETAILED DESCRIPTION OF THE INVENTION

Figure 1:
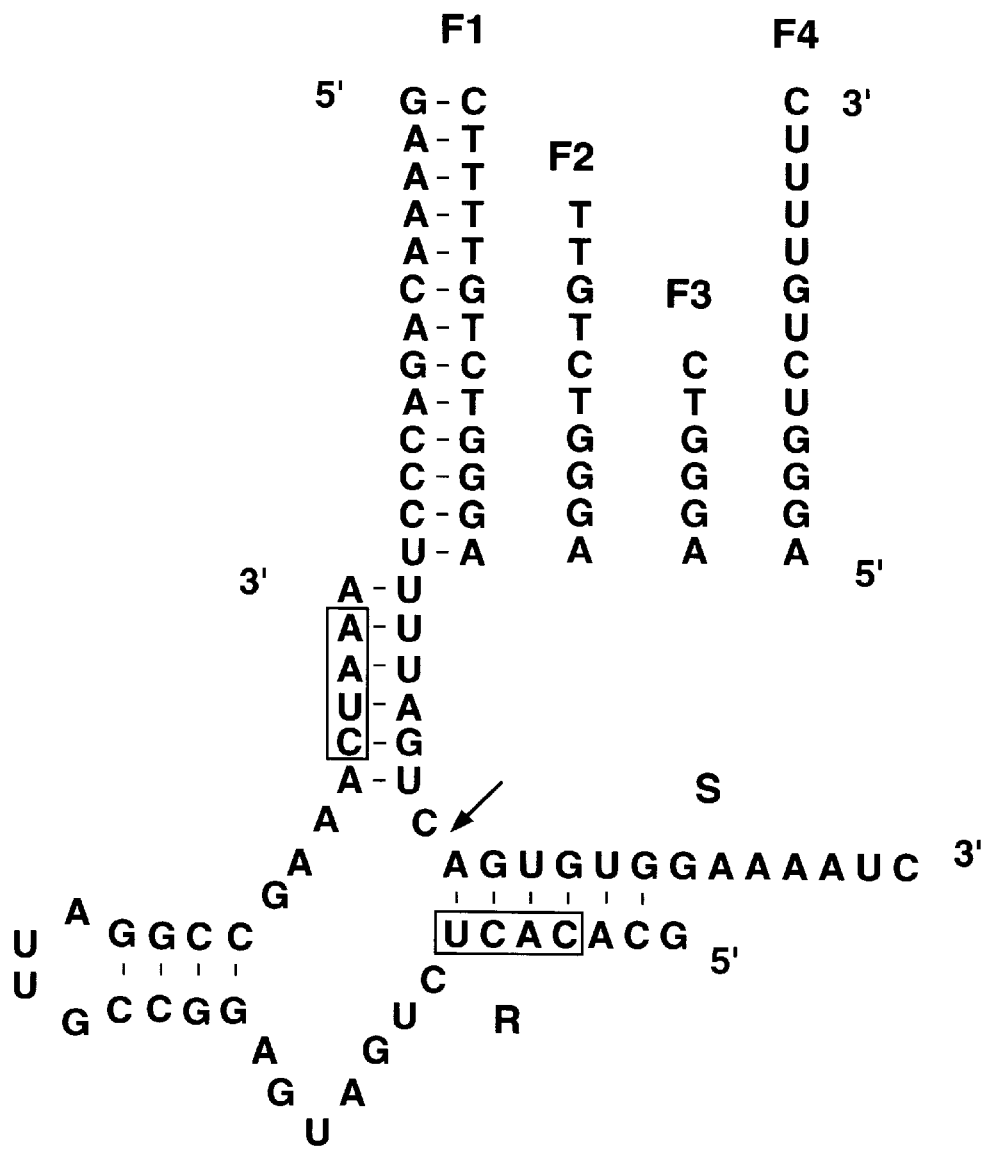
FIG. 1 shows the nucleotide sequences of substrate RNA (S, SEQ ID NO:1), ribozyme (R, SEQ ID NO:2) and facilitator oligodeoxy-nucleotides $F_1$ [SEQ ID NO:3], $F_2$ [SEQ ID NO:4], $F_3$ [SEQ ID NO:5], and facilitator oligoribonucleotide $F_4$ [SEQ ID NO:6] with the same sequence as $F_1$ [SEQ ID NO:3]. The site of cleavage of substrate is indicated by the arrow. Boxes indicate the positions of 2'-O-methyl nucleotides (when present).

The development of antiviral drugs based on RNA catalysts has been inhibited by the mutually limiting requirements of high specificity and RNA cleavage rate. Increased base pairing between a ribozyme and a substrate RNA has been shown to decrease the rate of RNA cleavage. In order for a ribozyme to discriminate between all RNAs in a cell, a ribozyme must form about 15 base pairs with the target. However, longer flanking sequences in ribozymes is related to decreased catalytic cleavage.

Moreover, this development has been hindered by the degradation of ribozymes by nucleases which takes place in cells.

It has been discovered that hammerhead ribozyme degradation by nucleases has been dramatically reduced while unexpectedly increasing ribozyme activity by modifying the ribozyme flanking sequences to contain a nucleotide having substituents on the oxygen at the 2'-position of the nucleotide; i.e., by introducing a 2'-O-substituted nucleotide into the ribozyme. Such a modification unexpectedly results in a significant overall increase in ribozyme catalytic activity.

The substituents on the nucleotide 2'-oxygen may be a lower alkyl group, lower alkenyl group, a phenyl alkyl group where the alkyl is lower alkyl, a phenyl alkenyl group where the alkenyl is lower alkenyl, an acyl group, or a phenylacyl group.

By lower alkyl in the present invention is meant straight or branched chain alkyl groups having 1–6 carbon atoms.

By lower alkenyl is meant straight or branched chain lower alkenyl having from 1–6 carbon atoms.

By acyl is meant radicals of the formula

where R is straight or branched chain lower alkyl having 1–6 carbon atoms.

By phenyl acyl is meant radicals of the formula

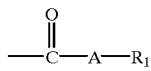

where A represents straight or branched chain lower alkylene having 1–6 carbon atoms; and $R_1$ represents phenyl.

The modified ribozymes of the present invention may be prepared on automated oligonucleotide synthesizers or enzymatically from templates. For example, the partially 2'-O-alkylated or acylated ribozymes may be prepared using an automated solid-support phosphoramidite method with commercial nucleoside phosphoramidites having either 2'-O-silyl, 2'-O-alkyl, or 2'-O-acyl groups. The modified ribozymes of the invention should be prepared such that the 2'-O-substituted nucleotides are located primarily in the flanking sequences. Those skilled in the art would recognize methods for preparing other 2'-O-substituted nucleotides.

Suitable synthetic methods for preparing various 2'-O-substituted nucleotides are disclosed by Iribarren et al., Proc. Natl. Acad. Sci. 87: 7747–7751 (1990); Sproat et al., Nucleic Acids Res. 19: 733–738 (1991); and Sproat et al., Nucleic Acids Res. 18: 41–49 (1989). These routes typically involve protecting the 3' and 5'-hydroxyl groups, and subsequently treating with an alkyl iodide in the presence of a strong organic base such as 2-tert-butylimino-2-diethylamino-1,3-dimethylperhydro-1,3,2-diazaphosphorphorin (BDDDP). Other alkylating agents such as diazomethane can also be used. In some situations, it will be necessary to protect reactive amino groups prior to alkylation or acylation.

By flanking sequence in the present invention is meant the sequence of nucleotides immediately adjacent to the core region of the ribozyme. The flanking sequence is that region of the ribozyme that base-pairs with the RNA substrate. Each ribozyme flanking sequence may comprise from about 3 to about 50 nucleotides.

The ribozymes modified to comprise 2'-O-substituted nucleotides may have either one or both of the flanking sequences modified to contain these nucleotides. Preferred modified ribozymes will have a 2'-O-substituted nucleotide in both franking sequences. Furthermore, each flanking sequence may comprise a single 2'-O-substituted nucleotide or may contain a plurality of these nucleotides. The number of modified nucleotides in the flanking sequence will vary from about 20% of the nucleotides being methylated to about 100%. A more preferred range is from 50% to about 100%.

It has also been unexpectedly discovered that rate of cleavage of substrate RNA by a modified ribozyme is further enhanced by introducing an oligonucleotide into the system which hybridizes immediately adjacent to the modified ribozyme. The facilitator oligonucleotides of the present invention are designed to bind to RNA sequences contiguous to flanking sequences of the ribozymes.

The facilitator oligonucleotides suitable for use in the instant invention may be either oligodeoxynucleotides or oligoribonucleotides. Furthermore, the facilitator oligonucleotide may be selected to bind to a sequence contiguous to the flanking sequence either at the 5' or the 3' side of the ribozyme. In addition, a combination of two facilitator oligonucleotides may be employed, where one facilitator is bound contiguously to the 3' flanking sequence and the other to the 5' flanking sequence. Alternatively, a plurality of facilitators may be employed to catalyze ribozyme activity. For example, in a system employing three facilitators, two facilitators could bind contiguously to the 3' flanking sequence, while a single additional facilitator could bind contiguously to the 5' flanking sequence. A variety of other combinations are possible.

The facilitator oligonucleotides of the present invention typically comprise between about 5 and 50 nucleotides. More preferred facilitator oligonucleotides comprise between about 5 and 15 nucleotides. Particularly preferred facilitators according to the invention comprise about 13 nucleotides. Selection of a facilitator of a specific length is related to the length of the ribozyme flanking sequences.

In addition, facilitator deoxynucleotides may be selected to have between about 5 and 50 nucleotides complementary to the RNA substrate sequence as well as additional nucleotides which are not complementary to the RNA sequence.

The specific facilitator oligonucleotides are synthesized to bind to the desired RNA sequences such that they are contiguous to the flanking sequences of various ribozymes that cleave related RNA sequences. As described here, the oligonucleotides can be synthesized on automated DNA synthesizers or from DNA templates.

The facilitator oligonucleotides may be synthesized such that they are not completely contiguous to the flanking sequence of the desired ribozyme. For example, the facilitator may be synthesized such that, when the ribozyme and facilitator oligonucleotide are bound to the substrate RNA, a small gap of from one to about five oligonucleotides exists between the ribozyme and the facilitator oligonucleotide. In preferred embodiments of the invention, the gap between the facilitator and the ribozyme will be between 0 (zero) and 2 nucleotides. The most preferred embodiment will have no nucleotide gap between the facilitator and the ribozyme.

The facilitator oligonucleotides may be synthesized and subsequently modified to include moieties which will influence the rate of substrate cleavage by ribozyme, increase uptake by cells, or increase resistance to degradation.

By increasing the number of bases of the substrate RNA bound near the cleavage site, facilitators permit use of faster acting ribozymes with shorter flanking sequences. In viral applications, facilitators might be of dual benefit in also directing cleavage of the viral RNA by endogenous ribonuclease H.

The present invention further provides compositions comprising a modified ribozyme.

The present invention also includes compositions which comprise a ribozyme and an effective amount of a facilitator oligonucleotide. In any treatment, however, the compositions comprising the 2'-O-methylated ribozyme, or the methylated ribozyme and facilitator oligonucleotide must be administered to individuals in a manner capable of delivering the oligonucleotide and ribozyme initially into the blood stream and subsequently into cells.

The compositions of the invention may be administered parenterally, orally, by inhalation or spray or rectally in dosage unit formulations containing conventional non-toxic pharmaceutically acceptable carriers, adjuvants and vehicles. The term "parenteral" as used herein includes subcutaneous injections, intravenous, intramuscular, intrasternal injection or infusion techniques. The compositions of the invention would be provided in a pharmaceutical formulation comprising the composition and a pharmaceutically acceptable carrier. In order for the compositions to be suitable for oral administration, oligonucleotides and ribozymes must be resistant to nucleases. Such resistance to nucleases may be imparted to the oligonucleotides by, for example, internucleotide phosphate modifications. Additional resistance to nucleases may also be bestowed on the modified ribozymes by internucleotide phosphate modification. Modified internucleotide phosphates suitable for use in the facilitator oligonucleotides and 2'-O-substituted ribozymes of the present invention include phosphorothioates, methylphosphonates, phosphoramidates, and phosphotriesters.

The amount of active composition that may be combined with the carrier materials to produce a single dosage form will vary depending upon the host treated and the particular mode of administration. It will be understood that the specific dose level for any particular patient will depend upon a variety of factors including the activity of the specific composition employed, the age, body weight, general health, sex, diet, time of administration, route of administration, severity of the particular disease undergoing therapy.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

1. Preparation of RNA Substrate

A synthetic RNA substrate strand (S, SEQ ID NO:1) was prepared to correspond to the sequence 146–173 in HIV-1 RNA. This RNA substrate strand was transcribed from synthetic DNA templates following a method described by Milligan and Uhlenbeck, Nucleic Acids Res. 15: 8783–8798 (1987), in a reaction containing Tris·HCl (40 mM, pH 8.1), $MgCl_2$ (6 mM), spermidine (1 mM), dithiothreitol (50 mM), bovine serum albumin (50 µg per ml), inorganic pyrophosphatase (4 units per ml), T7 RNA polymerase (4000 units per ml) and four ribonucleotide 5'-triphosphates (1 µM each) supplemented with $\alpha$-$^{32}$P-UTP (3000 Ci/mmol). After incubation at 37° C. for 2 hours, the RNA was purified by electrophoresis in 10% polyacrylamide gels containing 8 M urea. The radiolabeled RNA was quantitated using the specific activity of the incorporated $^{32}$P.

2. Preparation of Hammerhead Ribozyme

A hammerhead ribozyme (R, SEQ ID NO:2) designed to cleave RNA substrate strand S was prepared. The hammerhead ribozyme was prepared by automated chemical synthesis using standard phosphoramidite reagents. 2'-O-methylated ribozymes were prepared using the automated solid support phosphoramidite method with commercially available nucleoside phosphoramidites bearing either 2'-O-silyl or 2'-methyl groups as described by Sproat et al., Nucleic Acids Res. 17: 3373–3386 (1989). In addition, a 2'-deoxy derivative of ribozyme R [SEQ ID NO:2] was prepared having all the 2'-hydroxyl groups in the flanking sequences replaced by hydrogen. Products were purified by electrophoresis in 15% polyacrylamide gels containing 8M urea, eluted by crush and soak in 0.5M ammonium acetate, desalted and quantitated by UV absorption.

3. Preparation of Facilitator and Control Oligonucleotides

Facilitator oligonucleotides $F_1$ [SEQ ID NO:3], $F_2$ [SEQ ID NO:4], and $F_3$ [SEQ ID NO:5] were prepared to contain 13, 10, and 6 nucleotides respectively, and to hybridize to substrate S contiguously with ribozyme R [SEQ ID NO:2]. Facilitator oligoribonucleotide $F_4$ [SEQ ID NO:6] was prepared with the same sequence as $F_1$ [SEQ ID NO:3]. In addition, a control oligonucleotide having a random sequence was synthesized. The sequences of the facilitator oligonucleotides are shown in FIG. 1.

Both ribo- and deoxyribooligonucleotides were prepared by automated chemical synthesis utilizing essentially the same procedures set forth in part 2 of this Example.

EXAMPLE 2

1. Cleavage of Substrate RNA with Unmethylated Ribozyme

The cleavage of substrate RNA by ribozyme R [SEQ ID NO:2] was studied both with and without facilitator oligo $F_1$ [SEQ ID NO:3]. The cleavage of substrate RNA gave products $P_1$ and $P_2$ having chain lengths expected from cleavage at the site indicated in FIG. 1.

Figure 2A:
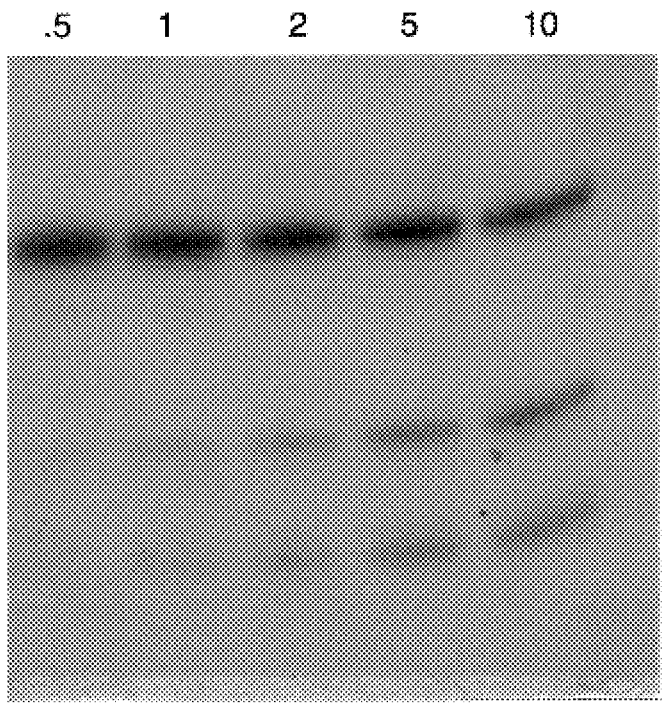
FIG. 2A is an autoradiograph showing the results of cleavage of radiolabelled substrate S [SEQ ID NO:1] by ribozyme R [SEQ ID NO:2] without facilitator oligonucleotide to give products $P_1$ and $P_2$ containing 20 and 13 nucleotides respectively.
Figure 2B:
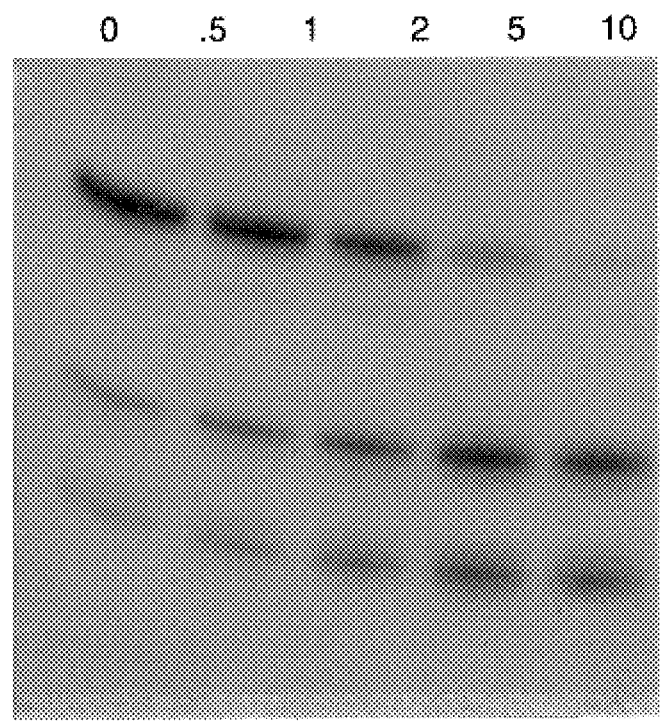
FIG. 2B is an autoradiograph showing the results of cleavage of radiolabelled substrate S [SEQ ID NO:1] by ribozyme R [SEQ ID NO:2] in the presence of facilitator oligonucleotide $F_1$ [SEQ ID NO:3] to give products $P_1$ and $P_2$ containing 20 and 13 nucleotides respectively.

The cleavage reactions were run as follows: a solution (45 µl) containing substrate (13.4 µM), ribozyme (0.67 µM) and facilitator where appropriate (20 µM) in 50 mM Tris·HCl (pH 7.4) was brought to 37° C. Reaction was initiated by the addition of $MgCl_2$ (5 µL, 200 mM). After times of 0.5, 1, 2, 5, and 10 minutes, aliquots of 5 µL were added to 15 µl of saturated urea:200 mM EDTA (1:1) and cooled to about −70° C. with dry ice to stop the reaction. The samples were then denatured by heating in formamide loading buffer at 90° C. for 3 minutes and subsequently analyzed alongside molecular weight markers by electrophoresis in 15% polyacrylamide gel containing 7M urea. The products were autoradiographed. The autoradiographs are shown in FIG. 2. Panel A shows the results of the cleavage reaction without any facilitator oligonucleotide and Panel B shows the results of cleavage with facilitator oligo $F_1$ [SEQ ID NO:3] present.

2. Cleavage of Substrate RNA with 2'-O-methylated Ribozyme

The cleavage of substrate RNA was studied using methylated and unmethylated ribozymes with and without facilitator $F_1$ [SEQ ID NO:3].

The cleavage reactions were run under substantially the same conditions as described above in part 1 of this example. Reactions contained 20 equivalents of substrate and 30 equivalents of facilitator relative to the methylated or unmethylated ribozyme.

Figure 4:
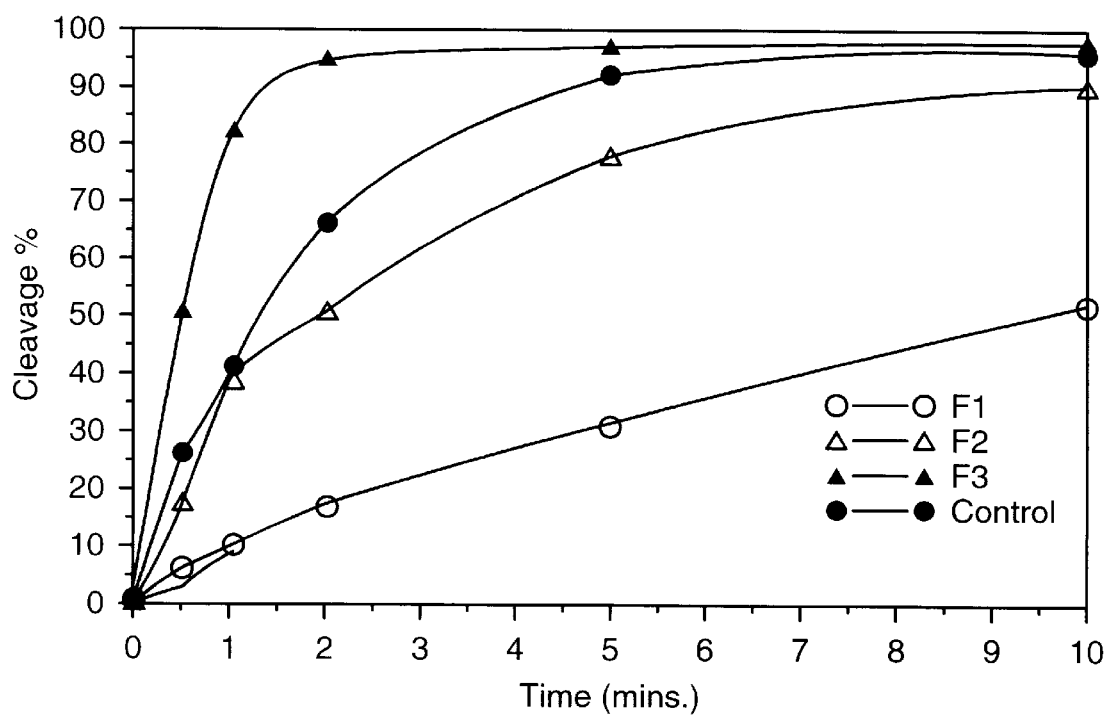
FIG. 4 is a graph showing the rates of cleavage by 2'-O-methylated and unmethylated ribozymes. Filled symbols indicate reactions with F, and open symbols those without. Circles indicate unmethylated ribozyme, triangles represent 2'-O-methylated ribozymes.

As shown in FIG. 4, the half-lives of the substrate without $F_1$ [SEQ ID NO:3], were 10 minutes with unmethylated ribozyme and 2 minutes with methylated ribozyme. When facilitator $F_1$ [SEQ ID NO:3] was utilized, half-lives were further reduced to 1.3 minutes and 0.5 minutes, respectively.

3. Cleavage of substrate RNA with 2'-Deoxy Ribozyme

The cleavage of substrate RNA was studied using the 2'-deoxy derivative of ribozyme R [SEQ ID NO:2] (prepared above in Example 1, part 2). Cleavage reactions were run under substantially the same conditions as described above in part 1 of this example. Under these conditions, the unmethylated parent ribozyme cleaved about 80% of the substrate; 2'-deoxy derivative cleaved only about 8% of the substrate.

EXAMPLE 3

Relation of Facilitator Length to Ribozyme Activity

Figure 3:
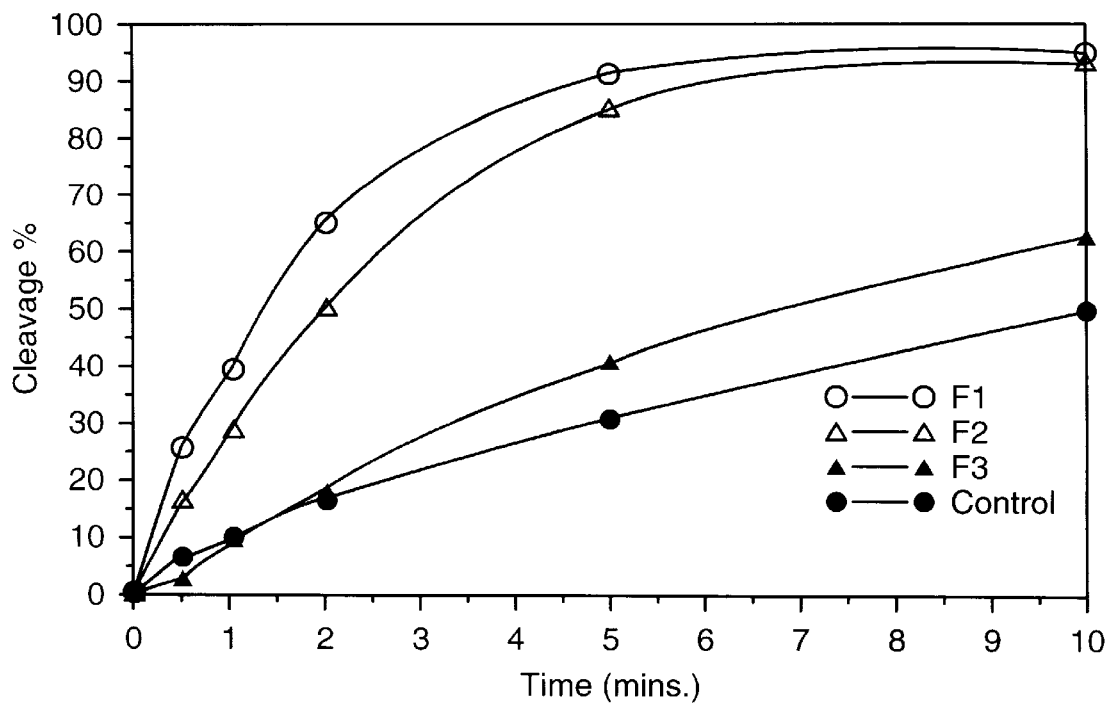
FIG. 3 is a graph of the time courses of cleavage reactions using facilitator oligonucleotides $F_1$ [SEQ ID NO:3], $F_2$ [SEQ ID NO:4], and $F_3$ [SEQ ID NO:5] and a control reaction with no facilitator oligonucleotide.

Cleavage of substrate RNA by ribozyme R was determined in the presence of facilitator oligonucleotides ($F_1$ [SEQ ID NO:3], $F_2$ [SEQ ID NO:4], $F_3$ [SEQ ID NO:5], and $F_4$ [SEQ ID NO:6]) of varying length. Cleavage reactions were run under conditions substantially similar to those employed in Example 2 above. Products and starting materials were quantitated for each time point. Autoradiograph gels were sliced and the materials on the slices quantitated by scintillation counting. The results of this experiment are graphically shown in FIG. 3.

Cleavage with no facilitator reached about 94% completion after about 160 minutes. The facilitator of 13 deoxynucleotides significantly reduced substrate half life. Table 1 shows the time required for ribozyme to cleave 10 equivalents of substrate at 37° C. The longest facilitator, $F_1$ [SEQ ID NO:3], reduced the half-life of substrate from 10 minutes to 1.3 minutes. The effects of facilitators $F_1$–$F_3$ [SEQ ID NOS:3–5] were inversely related to their lengths. A control oligonucleotide of the same length as $F_1$ [SEQ ID NO:3] had no effect on the rate.

In a separate experiment, it was found that oligodeoxyribonucleotide $F_1$ was more effective at catalyzing ribozyme activity than oligoribonucleotide $F_4$ [SEQ ID NO:6] having the same sequence.

TABLE 1

Half-Lives of Substrate in the Presence of Ribozyme and Facilitators

| Facilitator | $[S]_o^1$ | Half-Life (min) |
|---|---|---|
| none | 2.7 | 10 |
| F1[SEQ ID NO:3] | 2.7 | 1.3 |
| F2[SEQ ID NO:4] | 2.7 | 1.9 |
| F3[SEQ ID NO:5] | 2.7 | 6.9 |
| none | 0.9 | 40 |
| F1[SEQ ID NO:3] | 0.9 | 4.9 |
| F4[SEQ ID NO:6] | 0.9 | 12.3 |

[1]Starting concentrations of substrate ($\mu$M)

From the foregoing, it will appreciated that although specific embodiments of the invention have been described herein for purposes of illustration, various modifications may be made without deviating from the spirit or scope of the invention.

EXAMPLE 4

Ribozyme Resistance to Nuclease Degradation

Figure 5:
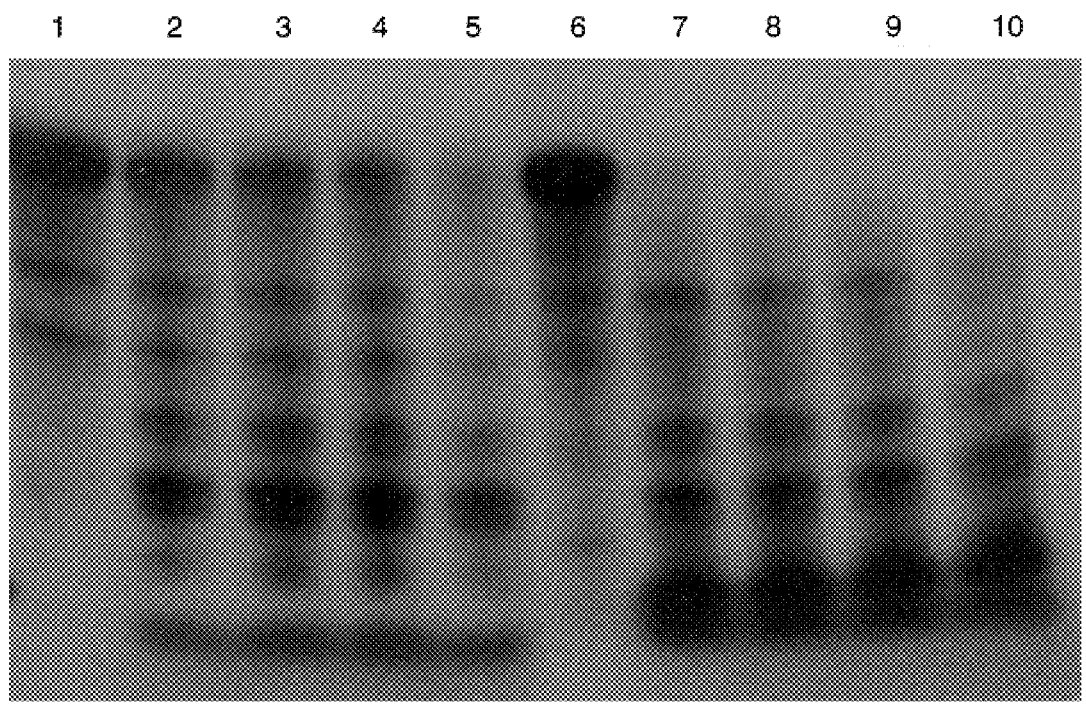
FIG. 5 is an autoradiograph showing the results of degradation of 2'-O-methylated and unmethylated ribozymes in 1% bovine fetal serum. Lane 1 is 2'-O-methylated ribozyme prior to incubation with bovine fetal serum. Lanes 2–5 show methylated ribozyme incubated with serum for 1, 6, 15, and 30 minutes, respectively. Lane 6 is unmodified ribozyme prior to incubation. Lanes 7–10 are unmodified ribozymes incubated with serum for 1, 6, 15, and 30 minutes, respectively.
Figure 6:
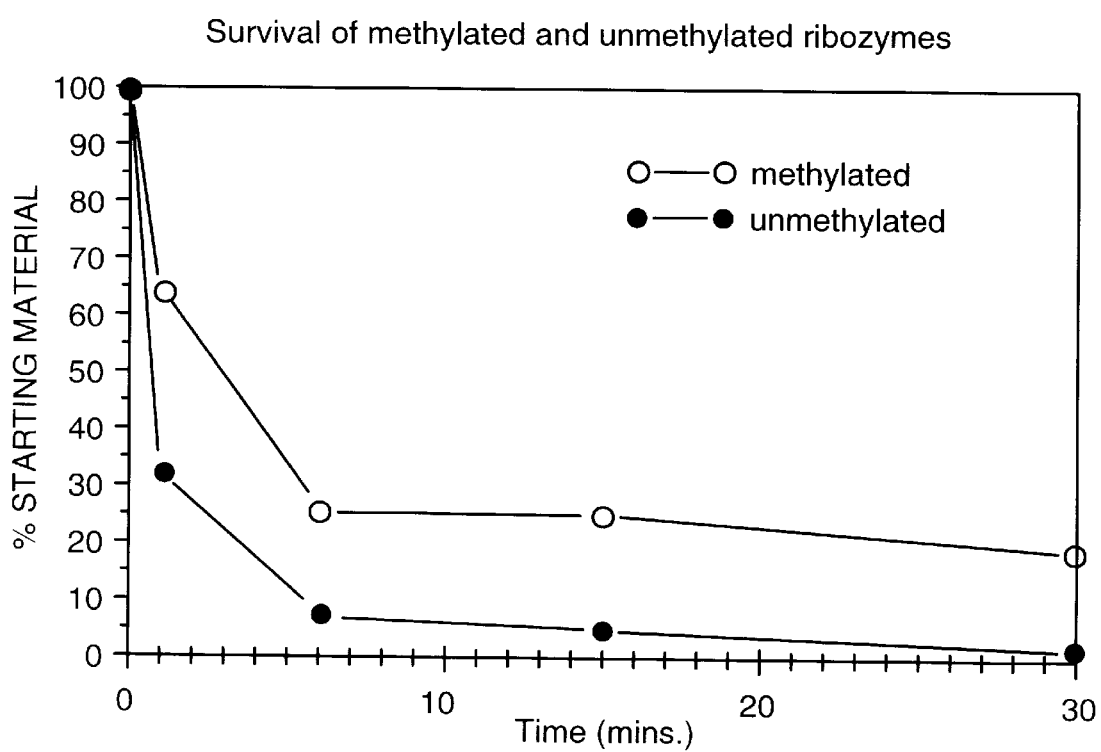
FIG. 6 is a graph of the survival of methylated and unmethylated ribozyme in Dulbecco's Modified Eagle's Medium containing 1% bovine fetal serum at 37° C.

The effect of ribozyme nucleotide modification on resistance to nuclease degradation was examined. Unmodified and 2'-O-methylated hammmerhead ribozymes (prepared in Example 1, part 2) were incubated in Dulbecco's Modified Eagle's Medium containing 1% bovine fetal serum at 37° C. Aliquots were withdrawn, analyzed by polyacrylamide gel electrophoresis, and autoradiographed. Bands were quantitated by scanning densitometry. The results are depicted in the autoradiograph shown in FIG. 5. Methylation of the 2'-oxygen in flanking sequence nucleotides reduced the rate of degradation of the ribozyme about four fold. Half-lives of the methylated (3 minute) and unmodified (0.8 minutes) ribozymes were determined from plots of the results, as shown in FIG. 6.

---

What is claimed is:

1. A hammerhead ribozyme having the sequences 5' GCA CAC UCU GAU GCC GUU AGG CCG AAA CUA AA 3' SEQ ID NO 7 where the nucleotides forming the 5' CACU 3' and 5' CUAA 3' sequences of the ribozyme are 2'-O-methyl nucleotides.

2. A method for increasing the catalytic activity of a ribozyme having the sequence 5' GCA CAC UCU GAU GAG GCC GUU AGG CCG AAA CUA AA 3' SEQ ID NO 8 comprising preparing the ribozyme to have 2'-O-methyl nucleotides in the 5' CACU 3' and 5' CUAA 3' sequences of the ribozyme.

3. A hammerhead ribozyme comprising one or more 2'-O-methyl substituted nucleotides in one or both of the ribozyme's flanking regions.

4. The hammerhead ribozyme according to claim 3, wherein the ribozyme's flanking region is from 3 to 10 nucleotides long.

5. The hammerhead ribozyme according to claim 3, wherein 20% or more of the nucleotides in the flanking sequences are 2'-O-methyl substituted.

6. The hammerhead ribozyme according to claim 3, wherein from 50% to 100% of the nucleotides in both flanking regions are 2'-O-methyl substituted.

7. A composition comprising a ribozyme according to claim 3 and a facilitator oligonucleotide.

8. The composition according to claim 7, wherein the facilitator oligonucleotide hybridizes with a sequence in a target RNA that is spaced no more than about three nucleotides from the target RNA to which the ribozyme hybridizes.

9. The composition according to claim 8, wherein the facilitator oligonucleotide is from about 5 to about 15 nucleotides long.

10. A hairpin ribozyme comprising one or more 2'-O-methyl substituted nucleotides in the ribozyme's flanking region.

11. The hairpin ribozyme according to claim 10, wherein the ribozyme's flanking region are from 3 to 10 nucleotides long.

12. The hairpin ribozyme according to claim 10, wherein 20% or more of the nucleotides in the flanking region are 2'-O substituted.

13. The hairpin ribozyme according to claim 10, wherein from 50% to 100% of the nucleotides in the flanking region are substituted.

14. A composition comprising a ribozyme according to claim 10 and a facilitator oligonucleotide.

15. The composition according to claim 14, wherein the facilitator oligonucleotide hybridizes with a sequence in a target RNA that is spaced no more than about three nucleotides from the target RNA to which the ribozyme hybridizes.

16. The composition according to claim 15, wherein the facilitator oligonucleotide is from about 5 to about 15 nucleotides long.

\* \* \* \* \*

SEQUENCE LISTING

<160> NUMBER OF SEQ ID NOS: 8

<210> SEQ ID NO 1
<211> LENGTH: 33
<212> TYPE: RNA
<213> ORGANISM: Human immunodeficiency virus type 1

<400> SEQUENCE: 1
gaaaacagac ccuuuuaguc aguuggaaa auc          33

<210> SEQ ID NO 2
<211> LENGTH: 35
<212> TYPE: RNA
<213> ORGANISM: Artificial Sequence
<220> FEATURE:
<223> OTHER INFORMATION: Description of Artificial Sequence:Hammehead
      ribozyme

<400> SEQUENCE: 2
gcacacucug augaggccgu uaggccgaaa cuaaa          35

<210> SEQ ID NO 3
<211> LENGTH: 13
<212> TYPE: DNA
<213> ORGANISM: Artificial Sequence

```
<220> FEATURE:
<223> OTHER INFORMATION: Description of Artificial Sequence:Facilitator
      oligonucleotide

<400> SEQUENCE: 3
agggtctgtt ttc                                                          13

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence:Facilitator
      oligonucleotide

<400> SEQUENCE: 4
agggtctgtt                                                              10

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence:Facilitator
      oligonucleotide

<400> SEQUENCE: 5 agggtc                                                                   6

<210> SEQ ID NO 6
<211> LENGTH: 13
<212> TYPE: RNA
<213> ORGANISM: Artificial Sequence
<220> FEATURE:
<223> OTHER INFORMATION: Description of Artificial Sequence:Facilitator
      oligonucleotide

<400> SEQUENCE: 6
agggucuguu uuc                                                          13

<210> SEQ ID NO 7
<211> LENGTH: 32
<212> TYPE: RNA
<213> ORGANISM: Artificial Sequence
<220> FEATURE:
<223> OTHER INFORMATION: Description of Artificial Sequence:Hammerhead
      ribozyme

<400> SEQUENCE: 7
gcacacucug augccguuag gccgaaacua aa                                     32

<210> SEQ ID NO 8
<211> LENGTH: 35
<212> TYPE: RNA
<213> ORGANISM: Artificial Sequence
<220> FEATURE:
<223> OTHER INFORMATION: Description of Artificial Sequence:Hammerhead
      ribozyme

<400> SEQUENCE: 8
gcacacucug augaggccgu uaggccgaaa cuaaa                                  35
```